US00PP10798P

United States Patent [19]

McGredy

[11] Patent Number: Plant 10,798

[45] Date of Patent: Feb. 23, 1999

[54] GRANDIFLORA ROSE PLANT NAMED 'MACYELKIL'

[75] Inventor: Sam McGredy, Auckland, New Zealand

[73] Assignee: DeVor Nurseries, Inc., Watsonville, Calif.

[21] Appl. No.: 742,143

[22] Filed: Oct. 31, 1996

[51] Int. Cl.[6] ..... A01H 5/00

[52] U.S. Cl. ..... Plt./15

[58] Field of Search ..... Plt./15, 24, 22

[56] References Cited

U.S. PATENT DOCUMENTS

P.P. 2,097 10/1961 Morey, Jr. ..... Plt./15

OTHER PUBLICATIONS

Upourom, Plant Variety Database, 1997/Mar., GTI Jouve Retrieval Software, Listing for 'Macyelkil'.

*Primary Examiner*—Howard J. Locker
*Attorney, Agent, or Firm*—Christie, Parker & Hale, LLP

[57] ABSTRACT

A grandiflora rose variety producing yellow flowers.

1 Drawing Sheet

BACKGROUND OF THE INVENTION

The present invention relates to a new and distinct grandiflora rose variety which was originated by my crossing as seed parent the variety known as 'Solitaire' and as pollen parent the variety known as 'Remember Me.' The varietal denomination of this new rose is 'Macyelkil.'

SUMMARY OF THE INVENTION

Among the novel characteristics possessed by this new variety which distinguish it from its parents and all other varieties of which I am aware are its attractive yellow flowers borne in trusses, which do not fade in the sun.

Asexual reproduction by budding of the new variety as performed in Watsonville, Calif., shows that the foregoing and other distinguishing characteristics come true to form and are established and transmitted through succeeding propagations. Other known forms of asexual reproduction for roses may be also employed.

Comparisons With Parents

The new variety has more petals and a longer bloom than 'Solitaire' and a deeper yellow coloration that does not fade in the sun. Flowers of 'Solitaire' are pale yellow with some pink color at the petal edges. 'Remember Me' produces flowers of unusual brownish yellow coloration.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.
*Seed parent.*—'Solitaire'.
*Pollen parent.*—'Remember Me'.
Class: Grandiflora.

The following is a detailed description of the new variety, from specimens grown outdoors in Watsonville, Calif., in the month of September. The color terminology used is in accordance with The Royal Horticultural Society Colour Chart (RHSCC), and refers to plate numbers in the aforementioned color chart. Phenotypic expression may vary depending on light, environmental and cultural conditions.

Flower

Blooming habit: Continuous.

A. Bud:
- (1) *Size.*—Medium; about 3.7 to 4 cm long, about 3.5 to 3.8 cm wide.
- (2) *Form.*—Globular.
- (3) *Color.*—When sepals first divide, bud color is near 46A.
- (4) *Sepals.*—Longer than bud, about 0.75 to 1 cm beyond bud. When bloom opens sepals straighten and then reflex. Color: Near 187A with edging of near 144B on top surface, somewhat lighter on undersurface.
- (5) *Peduncle.*—Length: about 3.5 to about 5 cm. Aspect: Smooth. Strength: Erect, medium. Color: Near 146B with some near 183C shading.
- (6) *Bracts.*—About 1 to 5. Either a single leaflet bract up to 3 leaflet bract; narrow and triangular in form; about 4 to 6 cm below flower.

B. Bloom:
- (1) *Size.*—Average size when fully expanded — about 10 to about 11 cm.
- (2) *Borne.*—7 to 13 blooms per stem.
- (3) *Form.*—Imbricated, slightly cupped, becoming ruffled at maturity.
- (4) *Petalage.*—Number of petals under normal conditions — about 34 to 36.
- (5) *Color* (1/3–1/2 *open*).—Outer petals — Top surface: near 14B; Undersurface: near 12A. Inner petals — Top surface: near 14A; Undersurface: 12A. Base of petals: Near 14B. General tonality from a distance: Deep yellow.
- (6) *Color* (*fully open*).—Outer petals — Top surface: near 9A; Undersurface; near 7A; some minor red blush on outer edge during later stages of the bloom. Inner petals — Top surface: near 12A; Undersurface: near 7A. Base of petals: Near 9A. General tonality from a distance: Deep yellow.
- (7) *Color change.*—A very slight lightening of color as bloom ages. Petal top surface Lightens very slightly. Petal undersurface Remains constant. General tonality at a distance Yellow.

C. Petals:
(1) *Texture.*—Thick, smooth.
(2) *Appearance.*—Inside matte and outside matte.
(3) *Form.*—Elliptic with slightly pointed tip.
(4) *Arrangement.*—Imbricated.
(5) *Petaloids.*—Many, about 9 to 11.
(6) *Fragrance.*—Slightly spicy.
(7) *Lasting quality.*—On plant about 12 to 14 days, about 5 to 7 days after cutting.
(8) *Persistence.*—Petals drop off cleanly.

Reproductive Organs

A. Stamens:
(1) *Arrangement.*—Irregularly arranged around styles.
(2) *Anthers.*—Color — near 12A.
(3) *Filaments.*—Color — near 17A.
(4) *Pollen.*—Color — near 17A.
B. Pistils:
(1) *Styles.*—Bunched, even.
(2) *Stigmas.*—Color — near 22A.
C. Characteristics of hips: Globose, about 1.5 cm wide by about 1.3 cm long, seeds do not protrude.

Plant

A. Form: Very upright.
B. Growth: Very vigorous; about 173 cm to about 203 cm in height at first season.
C. Foliage: Compound 3, 5 and 7 leaflets.
(1) *Size.*—Medium about 7 to 17 cm long, about 8 to 12 cm wide.
(2) *Quantity.*—Abundant.
(3) *Color.*—New foliage — upper side near 178B, underside near 178B; mature foliage — upper side near 147A, underside near 147B.
(4) *Shape*—Ovate.
(5) *Texture.*—Upper side slightly glossy and slightly leathery, thick; underside leathery, veiny.
(6) *Edge.*—Serrate.
(7) *Serration.*—Double serration edges.
(8) *Leaf stem.*—Color — medium green.
(9) *Stipules.*—Parallel, adnate, slightly bearded.
(10) *Rachis.*—Small prickles on underside.
(11) *Petioles.*—Top near 146A, underside near 146C.
(12) *Auricle.*—Pointed, curving outward slightly.
(13) *Resistance to disease.*—Moderate resistance to blackspot; good resistance to mildew and rust.
D. Wood:
(1) *New wood.*—Color near 144A with near 176A on side exposed to sun.
(2) *Old wood.*—Color near 144A, bark smooth.
E. Flower stem: About 70 cm to about 110 cm from last cut.
F. Thorns:
(1) *Thorns.*—Quantity: On main stalk, many thorns and prickles; laterals from stalk, many thorns but fewer prickles. Form: Thin, wide base. Length: About 1 to 1.2 cm long. Color: Near 184A with near 147D underneath. Position: Irregular.
(2) *Prickles.*—Profuse.
G. Winter hardiness: Winter hardy in Watsonville, Calif.

I claim:

1. A new and distinct variety of grandiflora rose plant, substantially as shown and described.

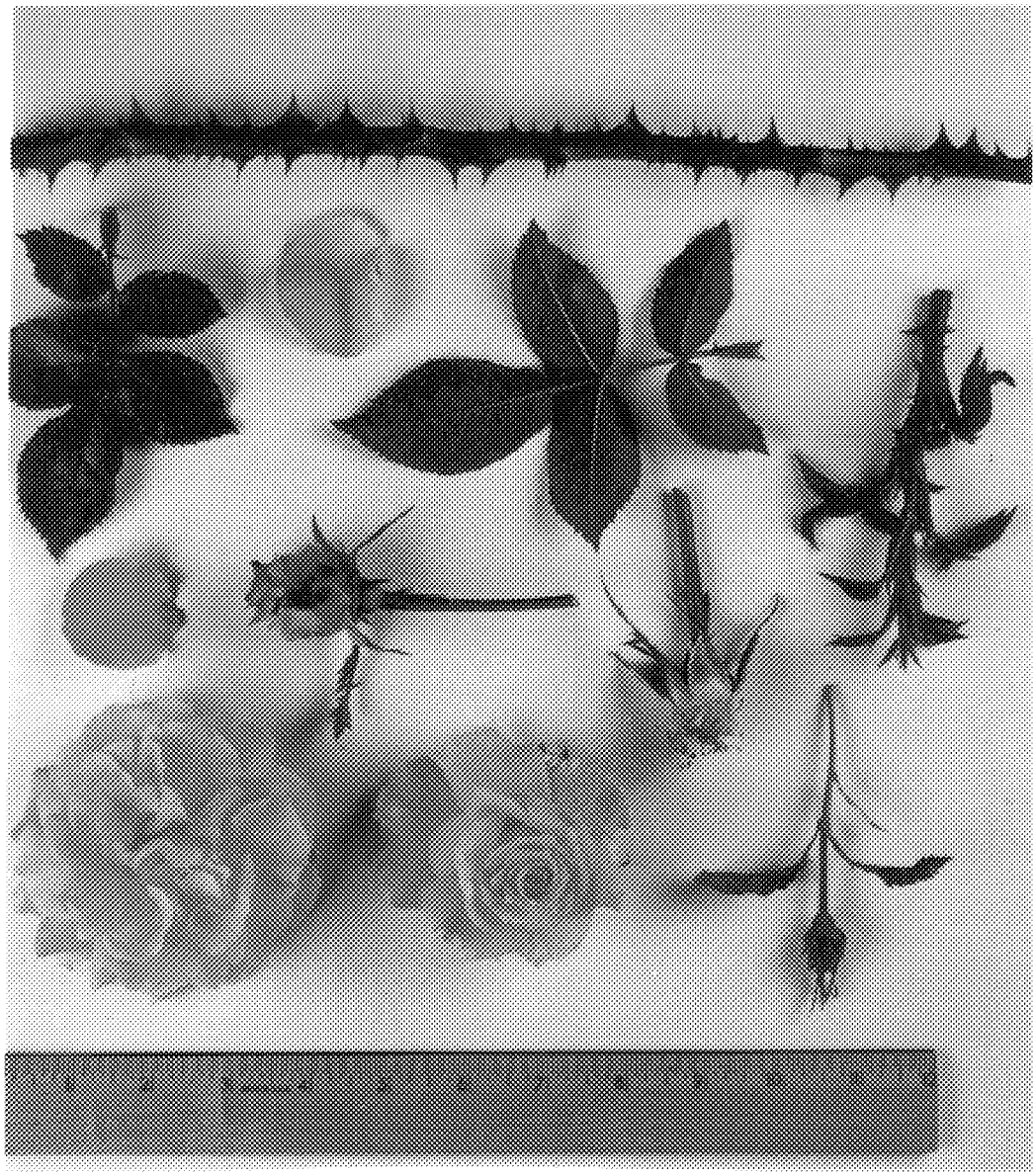

* * * * *